United States Patent [19]

Combs

[11] Patent Number: 5,116,837
[45] Date of Patent: May 26, 1992

[54] 2,9-DIHYDRO-(6 OR 7)-(3-OXO-2,3,4,5-TETRAHYDROPYRIDAZINYL)-PYRAZOLO (4,3-B)-1,4-BENZOXAZINES

[75] Inventor: Donald W. Combs, Piscataway, N.J.

[73] Assignee: Ortho Pharmaceutical Corporation, Paritan, N.J.

[21] Appl. No.: 631,560

[22] Filed: Dec. 21, 1990

[51] Int. Cl.⁵ .................. C07D 498/04; A61K 31/535
[52] U.S. Cl. ................................. 514/229.8; 544/101
[58] Field of Search ....................... 544/101; 514/229.8

[56] References Cited

U.S. PATENT DOCUMENTS

| | | | |
|---|---|---|---|
| 4,552,874 | 11/1985 | Mardin et al. | 546/64 |
| 4,721,784 | 1/1988 | Combs | 544/105 |
| 4,766,118 | 8/1988 | Combs | 514/224.2 |
| 4,923,869 | 5/1990 | Prücher et al. | 544/238 |
| 5,011,839 | 4/1991 | Tanikawa et al. | 544/238 |

Primary Examiner—Mukund J. Shah
Assistant Examiner—Philip I. Datlow
Attorney, Agent, or Firm—Benjamin F. Lambert

[57] ABSTRACT

The invention relates to novel compounds, 2,9-dihydro(6 or 7)-3-oxo-2,3,4,5-tetrahydropyridazinyl)-pyrazolo[4,3-b]benzoxazines. The claimed compounds are inhibitors of phosphodiesterase fraction III and have potent positive inotropic activity. These compounds are useful as cardiotonics or platelet aggregation inhibitors.

This invention also pertains to compositions comprising an effective amount of the compounds, to methods for preparing the claimed compounds and to methods for treating a mammal with the compounds.

9 Claims, No Drawings

2,9-DIHYDRO-(6 OR 7)-(3-OXO-2,3,4,5-TETRAHYDROPYRIDAZINYL)-PYRAZOLO (4,3-B)-1,4-BENZOXAZINES

1. FIELD OF THE INVENTION

The invention relates to novel compounds, 2,9-dihydro-(6 or 7)-(3-oxo-2,3,4,5-tetrahydropyridazinyl)-pyrazolo[4,3-b]-1,4-benzoxazines, of the formula

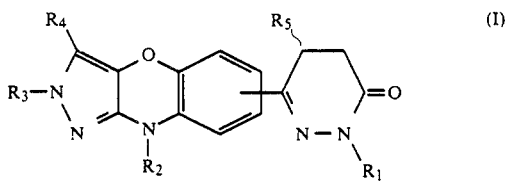

as further defined herein. The claimed compounds are inhibitors of phosphodiesterase fraction III and have potent positive inotropic activity. These compounds are useful as cardiotonics or platelet aggregation inhibitors.

This invention also pertains to compositions comprising the compounds, to methods for preparing the claimed compounds and to methods for treating a mammal with the compounds.

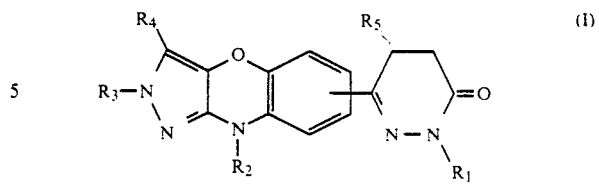

wherein $R_1$, $R_2$ and $R_3$ are each independently selected from the group consisting of H, $C_{1-6}$ straight-chain or branched-chain alkyl, $C_{3-6}$ cycloalkyl and $C_{3-6}$ alkenyl; and $R_4$ and $R_5$ each is selected from the group consisting of H, $C_{1-6}$ straight-chain or branched-chain alkyl, and $C_{3-6}$ cycloalkyl, and provided that where $R_1$, $R_2$ and $R_3$ each independently is other than H, the nitrogen is bonded to a carbon in $R_1$, $R_2$ and $R_3$ other than an unsaturated carbon, and that the C-6 of the pyridazinone moiety in the compound is attached at the C-6 or C-7 of the benzoxazine ring moiety in the compound.

In addition, the compounds of formula I, depending on the type of substitution, can exist in a number of tautomeric forms, in individual enantiomeric forms or as a racemate:

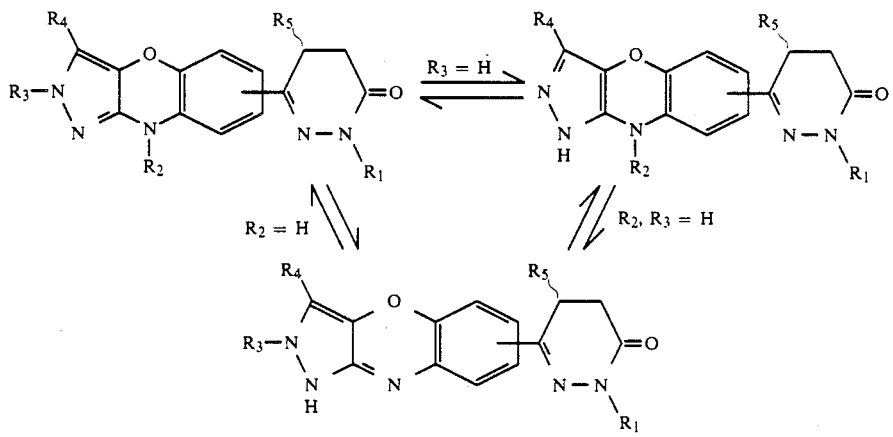

2. BACKGROUND OF THE INVENTION

The pyrazolo[4,3-b]-1,4-benzoxazine ring system has been described in the literature. The basic unsubstituted ring system is described by M. Mazharuddin and G. Thyagarajan (Tetrahedron Letters, 307 (1971)). Substituted analogs are described in a German Patent by Bayer A. G. (DE 3,204,126) wherein the compounds are described as lipoxygenase inhibitors and anti-inflammatory agents. There are no reports of a pyrazolobenzoxazine ring system having rings of any kind attached to it.

SUMMARY OF THE INVENTION

The present invention is directed to novel compounds, 2,9-dihydro-(6 or 7)-(3-oxo-2,3,4,5-tetrahydropyridazinyl)-pyrazolo[4,3-b]-1,4-benzoxazines, of the general formula:

The compounds of formula I are useful as cardiotonic agents having a long duration of activity and are very potent inhibitors of phosphodiesterase fraction III.

The invention also includes pharmaceutical compositions in which a novel compound of the present invention is the active ingredient, methods for preparing the compounds and methods for treating a mammal with the compounds.

4. DETAILED DESCRIPTION OF THE INVENTION

The invention in its broadest aspects relates to 2,9-dihydro-(6 or 7)-(3-oxo-2,3,4,5-tetrahydropyridazinyl)-pyrazolo[4,3-b]-1,4-benzoxazine compounds which exhibit cardiotonic activity, vasodilating activity, platelet aggregating inhibitory activity and phosphodiesterase fraction III inhibitory activity. The compounds demonstrating these activities are shown by formula I above, wherein C-6 of the pyridazinone moiety in the compound is attached at the C-6 or C-7 of the benzoxazine ring moiety in the compound.

The $C_{1-6}$ straight-chain or branched-chain alkyl moiety includes such groups as methyl, ethyl, isopropyl or tert-butyl, the $C_{3-6}$ cycloalkyl moiety includes such groups as cyclopropyl, cyclohexyl or methylcyclopentyl and the $C_{3-6}$ alkenyl moiety includes such groups as propenyl, methylpropenyl or butenyl.

The preferred compounds made by the present invention are those wherein $R_1$, $R_2$, $R_3$ and $R_4$ are hydrogen and $R_5$ is H or $CH_3$.

The compounds of formula I can be prepared as shown in Scheme I.

esterification is accomplished by suspending 1 in a lower ($C_{1-6}$) alkanol, R'OH, such as methanol or ethanol and then adding thereto a lower alkanoyl halide such as for example acetyl chloride. The reaction is effected from about 22° C. to about reflux temperature in about 0.5 hour to about 3 days.

Compound 1 is alternately esterified under acidic conditions in an acidified alcoholic solution. An acid such as HCl, $H_2SO_4$ or p-toulenesulfonic acid is employed to acidify the lower alkanol solvent, wherein the acid is used in about 5 to about 10 weight % to the

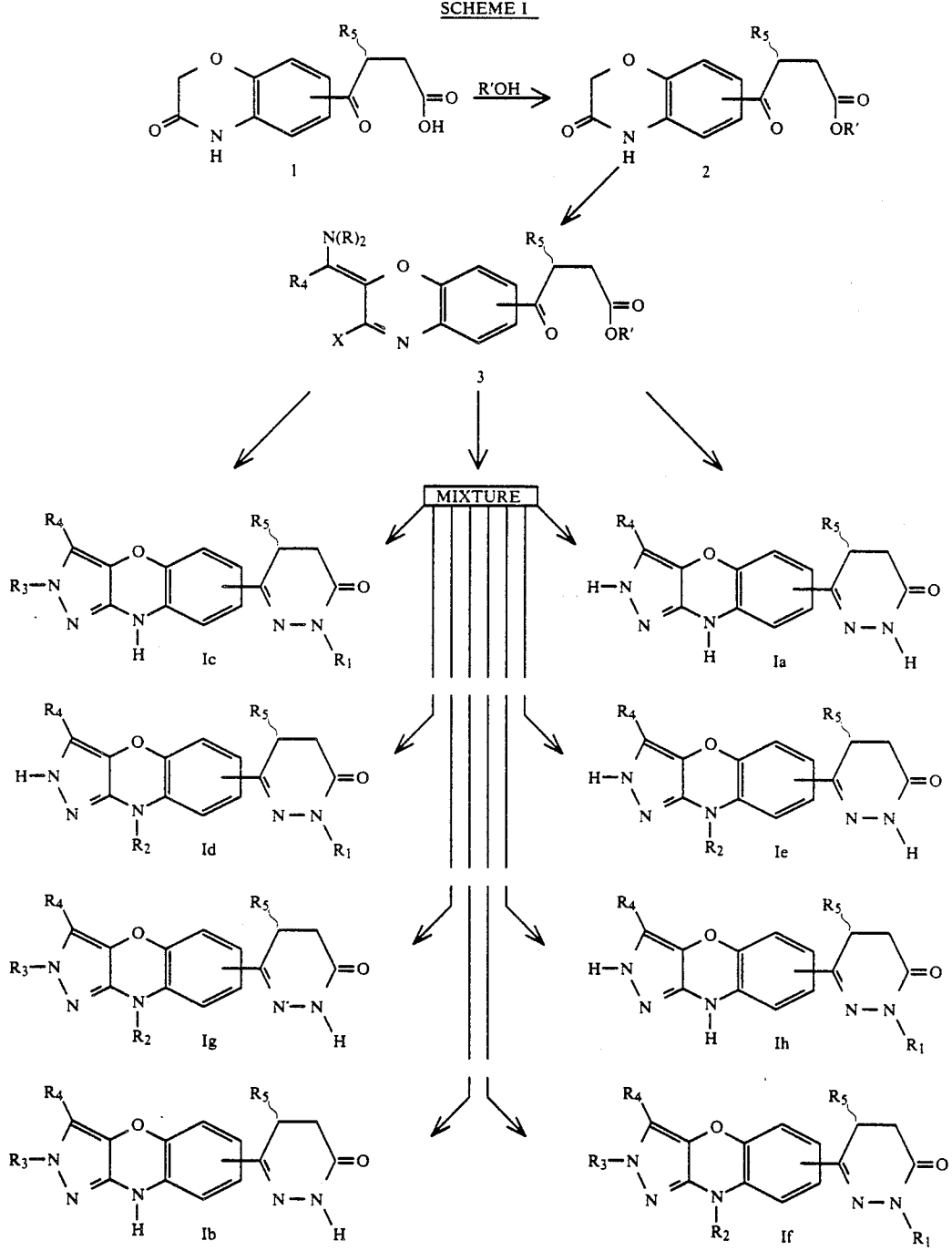

SCHEME I

In the first step of the synthesis, a 4-oxo-4-(3,4-dihydro-3-oxo-2H-1,4-benzoxazin-(6 or 7)-yl)butyric acid 1, is esterified under acidic conditions to yield 2. The carboxylic acid, or where a strong acid ion exchange resin is placed in the lower alkanol solvent, wherein the resin is used in about 10 to about 30 weight % to the carboxylic acid. The reaction is effected at about reflux temperature in about 1.5 hours to about 4 hours. In some instances the water that is formed during the esterification process is optionally removed by adding another organic liquid such as benzene or toluene to form an azeotrope.

Compound 2 is then reacted with a Vilsmeier reagent, a formylating reagent, to yield 3. The reagent is prepared by combining a compound (e.g., phosphoryl chloride, phosphoryl bromide, oxalyl chloride, bromine adduct of triphenylphosphine, phosgene or phosphene iminium chloride), which is the source of the halide, X that is introduced on 3, and a compound of the formula $(R)_2NCYR_4$ wherein Y is O or S, R is the same or different group selected from the group consisting of H, $C_{1-3}$ alkyl and phenyl and $R_4$ is as defined above (e.g., $(R)_2NCYR_4$ is N,N-dimethylformamide, N,N-dimethylthioformamide or N,N-dimethylacetamide). This reaction is carried out without a solvent or in a halogenated or a similarly inert solvent such as chloroform, dichloromethane, ethylene dichloride, carbon tetrachloride or dichlorobenzene. The reaction is carried out at about reflux temperature for about 2 hours to about 7 hours. Following the refluxing, the reaction mixture is then stirred for about 2 hours to about 24 hours.

Compound 3 is converted to Ia or Ic by heating 3 in a suitable solvent to about reflux temperature for about 1 hour to about 8 hours with 2 or more equivalents of a hydrazine of the formula $R''HN-NH_2$ wherein $R''$ is defined as $R_1$ and $R_3$ above. Where Ic is prepared by this reaction of 3 with $R''HN-NH_2$ wherein $R''$ is other than H, $R_1$ and $R_3$ and Ic are the same. This reaction is carried out in an aqueous or a lower alkanol solution, wherein an alkanol such as methanol, ethanol or isopropanol is employed. The reaction is also carried out with neat $R''HN-NH_2$.

Compounds I(b-h) are prepared by treating Ia with an alkylating agent. In particular, Ia is treated with an alkali metal base such as sodium hydride in an inert solvent such as dimethylformamide or dimethylsulfoxide to form a corresponding alkali salt compound as shown in FIG. 1. The salt is then reacted with an aliphatic

FIGURE 1

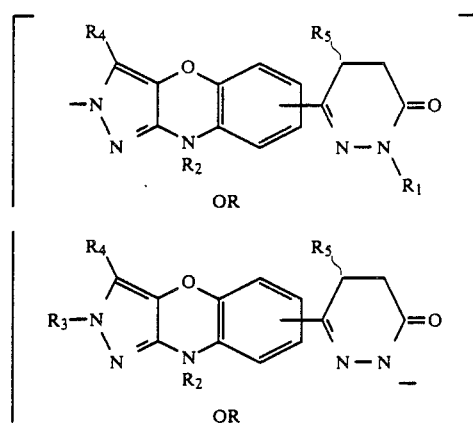

-continued
FIGURE 1

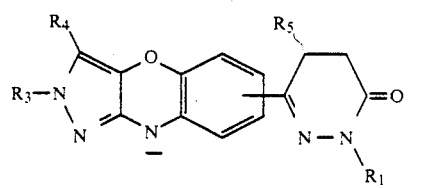

halide of the formula $R''X_1$: wherein $R''$ is defined as $R_1$, $R_2$ and $R_3$ above the proviso that it is not H; $X_1$ is selected from the group consisting of chloride, bromide and iodide; and $X_1$ is bonded to a carbon in $R''$ other than an unsaturated carbon. The reaction occurs at about 0° C. to about 40° C. in about 0.5 hour to about 8 hours to yield a mixture of compounds I(b-h) and unreacted Ia. The mixture is then worked-up by standard procedures (e.g., chromatography such as HPLC or crystallization) to isolate the individual N-alkylated compounds I(a-h). The compounds I(a-e & g-h) are subject to being alkylated as described above to yield the compounds of formula I.

Compound I, wherein $R_5$ is other than H, is obtained as a racemic mixture. The racemic mixture of I, is separated into its pure enantiomers by loading the mixture dissolved in a water miscible organic solvent such as dimethylsulfoxide onto an HPLC. column packed with chiral $\beta$-cyclodextrin and eluting the column with a buffered aqueous alcholic mixture. In addition, the use of other conventional resolution techniques such as fractional recrystallization, i.e., where a resolving agent is employed, are useful.

The starting materials, 4-oxo-4-(3,4-dihydro-3-oxo-2H-1,4-benzoxazin-(6 or 7)-yl)butyric acids, for preparing the 2,9-dihydro-(6 or 7)-(3-oxo-2,3,4,5-tetrahydropyridazinyl)-pyrazolo[4,3-b]-1,4-benzoxazines are prepared by methods described in U.S. Pat. Nos. 4,721,784 and 4,766,118, which are incorporated herein by reference.

The pharmaceutical compositions of this invention containing an effective amount of a compound of the formula I as the active ingredient in intimate admixture with a pharmaceutical carrier can be prepared according to conventional pharmaceutical compounding techniques. The carrier may take a wide variety of forms depending on the form of preparation desired for administration e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, although other ingredients, for example, to aid solubility or for perservative purposes, may be included. Injectable suspensions may also be prepared, in which case appropriate liquid carriers suspending agents and the like may be employed. The pharmaceutical compositions will generally contain in dosage unit form, e.g.tablet, capsule, powder,injection, teaspoonful and the like, from about 0.001 to about 10 mg/kg, and preferably from about 0.01 to about 0.1 mg/kg of the active ingredient.

The following examples describe the invention in greater particularity and are intended to be a way of illustrating but not limiting the invention.

5. EXAMPLES

Preparation of
2.9-Dihydro-6-(5-methyl-3-oxo-2,3,4,5-tetrahydropyridazin-6-yl)pyrazolo 4,3-b]-1,4-benzoxazine Step a: Methyl 4-oxo-4-(3,4-dihydro-3-oxo-2H-1,4-benzoxazin-7-yl)-3-methylbutyrate 4-Oxo-4-(3,4-dihydro-3-oxo-2H-1,4-benzoxazin-7-yl)-3-methylbutyric acid (5 g) was suspended in methanol (50 ml) and acetyl chloride (0.5 ml) added. The mixture was heated on a steam bath until all of the solid dissolved. The solvent was evaporated at reduced pressure providing the ester as a white foam which was recrystallized from ethyl acetate-methanol to give the product as white crystals, yield 5 g, mp 95°–98° C.

$C_{14}H_{15}NO_5$, Theor.: C, 60.63; H, 5.46; N, 5.05,
Found: C, 60.72; H, 5.52; N, 5.17.

Step b: Methyl 4-oxo-4-(3-chloro-2-dimethylaminomethylene-2H-1,4-benzoxazin-7-yl) -3-methylbutyrate Methyl 4-oxo-4-(3,4-dihydro-3-oxo-2H-1,4-benzoxazin-7-yl)-3-methylbutyrate (10 g) was added to chloroform (100 ml) containing $POCl_3$ (3.5 ml) and dimethylformamide (2.8 ml) at 0° C. The mixture was heated at reflux for 3 hours then stirred at room temperature overnight. The solvent was removed at reduced pressure, the residue was basified with 10% NaOH solution and extracted with ethyl acetate. The organic layer was washed with brine, dried over $MgSO_4$, filtered and evaporated to dryness. The residue was chromatographed on silica gel and eluted with methylene chloride. The fractions containing the Product were evaporated to dryness and the residue used without further purification.

Step c: 2,9-Dihydro-6-(5-methyl-3-oxo-2,3,4,5-tetrahydropyridazin-6-yl) pyrazolo[4,3-b]-1,4-benzoxazine Anhydrous hydrazine (2 equiv) was added to methyl 4-oxo-4-(3-chloro-2-dimethylaminomethylene-2H-1,4-benzoxazin-7-yl)-3-methylbutyrate (2.5 g) in ethanol (100 ml). After heating the resulting solution at reflux for 1 hour, the product was isolated by filtration as tan crystals and washed with ethanol to yield 1.65 g of the titled compound: mp 304°–306° C.; ms, (M+H)=284.

$C_{14}H_{13}N_5O_2$, Theor.: C, 59.35; H, 4.63; N, 24.73.
Found: C, 58.96; H, 4.63; N, 24.64.

EXAMPLE 2: Cardiotonic Activity

The cardiotonic activity of the compounds of formula is determined in accordance with the method of Alousi, A. A., et al., *J. Cir. Res.* 45, 666 (1979). Adult mongrel dogs were anesthetized with sodium pentobarbital 45 mg/kg, i.p.) and artifically respired. Mean arterial pressure (MAP) was recorded from a cannulated femoral artery and drugs are infused into a cannulated femoral vein. The arterial pressure pulse was used to trigger a cardiotachometer for determination of heart rate (HR). A right thoracotomy was performed and myocardial contractile force (CF) was measured with a Walton Brodie strain gauge sutured to the right ventricle. The ventricular muscle was stretched to produce a baseline tension of 100 g. A standard dose of dopamine (10–15 μg/kg/minutes for 3 minutes) was administered to determine myocardial responsiveness to inotropic stimulation.

Test compound was solubilized in a small volume of DMF diluted to a final concentration of 10% in physiological saline. Vehicle was tested in appropriate volumes and found to exert less than a 5% effect on contractile force. Compound was administered by infusion pump (one drug per animal) at rates of 0.58–2.2 ml/minute in three to four stepwise increasing doses. Each dose was infused over 5 minutes immediately after the effect of the previous dose peaked. MAP, HR, and CF responses were continuously monitored on a Beckman or Gould recorder and expressed as a percent change from pre-drug control values vs. the cumulative dose of drug administered. Quantitation of the inotropic potency was obtained by calculation of the contractile force (CF) $ED_{50}$. This was defined as the dose of compound that produced a 50% increase above baseline in myocardial contractile force. The values were obtained from the dose-response relationships either qraphically or by regression analysis.

2,9-Dihydro-6-(5-methyl-3-oxo-2,3,4,5-tetrahydropyridazin-6-yl) pyrazolo[4,3-b]-1,4-benzoxazine, a representative example of a compound of the formula I, had an intravenous $ED_{50}$ of 15 μg/kg in the anesthetized dog model with a maximum increase in cardiac force of 256% at a dose of 75 μg/kg.

I claim:

1. A compound of the formula

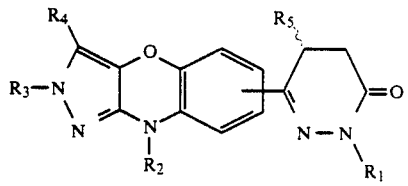

wherein
$R_1$, $R_2$ and $R_3$ are each independently selected from the group consisting of H, $C_{1-6}$ straight-chain or branched-chain alkyl, $C_{3-6}$ cycloalkyl and $C_{3-6}$ alkenyl; and $R_4$ and $R_5$ each is selected from the group consisting of H, $C_{1-6}$ straight-chain or branched-chain alkyl and $C_{3-6}$ cycloalky, and provided that were $R_1$, $R_2$ and $R_3$ each independently is other than H, the nitrogen is bonded to a carbon in $R_1$, $R_2$ and $R_3$ other than an unsaturated carbon, and that the C-6 of the pyridazinone moiety in the compound is attached at the C-6 or C-7 of the benzoxazine ring moiety in the compound.

2. The compound of claim 1 wherein $R_1$, $R_2$, $R_3$ and $R_4$ each is H and $R_5$ is $C_{1-6}$ straight-chain or branched-chain alkyl or H.

3. The compound of claim 2 which compound is 2,9-dihydro-6-(5-methyl-3-oxo-2,3,4,5-tetrahydropyridazine-6-yl)pyrazolo]4,3-b-]-1,4-benzoxazine.

4. A pharmaceutical composition comprising an effective amount of a compound of claim 1, as the active ingredient dispersed in a pharmaceutically acceptable carrier.

5. The composition of claim 4 wherein the compound is 2,9-dihydro-6-(5-methyl-3-oxo-2,3,4,5-tetrahydropyridazine-6-yl) pyrazolo]4,3-b]-1,4-benzoxazine.

6. A method of increasing the contractile force of a cardiac muscle in a mammal which comprises adminsitering to said mammal an effective amount of a compound of claim 1.

7. The method of claim 6 wherein the compound is 2,9dihydro-6-(5-methyl-3-oxo-2,3,4,5-tetrahydropyridazin-6-yl)pyrazolo]4,3-b]-1,4-benzoxazine.

8. A method of stimulating vasodilation in a mammal which comprises administering to said mammal an effective amount of a compound of claim 1.

9. The method of claim 8 wherein the compound is 2,9dihydro-6-(5-methyl-3-oxo-2,3,4,5-tetrahydropyridazin-6-yl)pyrazolo]4,3-b]-1,4-benzoxazine.

* * * * *

UNITED STATES PATENT AND TRADEMARK OFFICE
CERTIFICATE OF CORRECTION

PATENT NO. : 5,116,837

DATED : May 26, 1992

INVENTOR(S) : Donald W. Combs

It is certified that error appears in the above-identified patent and that said Letters Patent is hereby corrected as shown below:

Column 8, line 63-64 "tetrahydropyridazine"
Should be --tetrahydropyridazin--

Column 8, line 64 "]4,3-b[" should be --[4,3-b]--

Column 9, line 4 "tetrahydropyridazine" should be --tetrahydropyridazin--
Column 9, line 4 "]4,3-b]" should be --[4,3-b]--

Column 10, line 2 "2,9 dihydro" should be --2,9-dihydro--
Column 10, line 3 "]4,3-b]" should be --[4,3-b]--
Column 10, line 8 "2,9 dihydro" should be --2,9-dihydro--
Column 10, line 9 "]4,3-b]" should be --[4,3-b]--

Signed and Sealed this

Tenth Day of August, 1993

Attest:

MICHAEL K. KIRK

*Attesting Officer*  *Acting Commissioner of Patents and Trademarks*